(12) United States Patent
Ingber et al.

(10) Patent No.: US 9,220,831 B2
(45) Date of Patent: Dec. 29, 2015

(54) DEVICE AND METHOD FOR COMBINED MICROFLUIDIC-MICROMAGNETIC SEPARATION OF MATERIAL IN CONTINUOUS FLOW

(75) Inventors: Donald E. Ingber, Boston, MA (US); Shannon Xia, San Jose, CA (US); Tom P. Hunt, Oakland, CA (US); Robert M. Westervelt, Lexington, MA (US)

(73) Assignees: CHILDREN'S MEDICAL CENTER CORPORATION, Boston, MA (US); PRESIDENT AND FELLOWS OF HARVARD COLLEGE, Boston, MA (US)

( * ) Notice: Subject to any disclaimer, the term of this patent is extended or adjusted under 35 U.S.C. 154(b) by 1749 days.

(21) Appl. No.: 12/088,975

(22) PCT Filed: Oct. 6, 2006

(86) PCT No.: PCT/US2006/039344
§ 371 (c)(1),
(2), (4) Date: Sep. 23, 2008

(87) PCT Pub. No.: WO2007/044642
PCT Pub. Date: Apr. 19, 2007

(65) Prior Publication Data
US 2009/0220932 A1 Sep. 3, 2009

Related U.S. Application Data

(60) Provisional application No. 60/724,117, filed on Oct. 6, 2005.

(51) Int. Cl.
*G01N 15/14* (2006.01)
*A61M 1/36* (2006.01)
*B03C 1/28* (2006.01)

(52) U.S. Cl.
CPC .............. *A61M 1/36* (2013.01); *A61M 1/3618* (2014.02); *B03C 1/288* (2013.01);
(Continued)

(58) Field of Classification Search
CPC .......... G01N 15/1459; G01N 15/1484; G01N 15/1463; A61M 1/36; A61M 1/3618
See application file for complete search history.

(56) References Cited

U.S. PATENT DOCUMENTS 5,236,824 A * 8/1993 Fujiwara et al. .................. 435/5
(Continued)

FOREIGN PATENT DOCUMENTS

WO 2010123594 A2 10/2010
(Continued)

OTHER PUBLICATIONS

Inglis, D.W., et al., "Continuous Microfluidic Immunomagnetic Cell Separation," Applied Physics Letters, 85 (21):5093-5095 (2004).
Blankenstein, "Microfabricated flow system for magnetic cell and particle separation", Scientific and Clinical Applications of Magnetic Carriers,1997, 233-245.
(Continued)

Primary Examiner — Melanie Y Brown
(74) Attorney, Agent, or Firm — Nixon Peabody LLP

(57) ABSTRACT

A miniaturized, integrated, microfluidic device pulls materials bound to magnetic particles from one laminar flow path to another by applying a local magnetic field gradient. The device removes microbial and mammalian cells from flowing biological fluids without any wash steps. A microfabricated high-gradient magnetic field concentrator (HGMC) is integrated at one side of a microfluidic channel. When magnetic particles are introduced into one flow path, they remain limited to that flow path. When the HGMC is magnetized, the magnetic beads are pulled from the initial flow path into the collection stream, thereby cleansing the fluid. The microdevice allows large numbers of beads and materials to be sorted simultaneously, has no capacity limit, does not lose separation efficiency as particles are removed, and is useful for cell separations from blood and other biological fluids. This on-chip separator allows cell separations to be performed in the field outside of hospitals and laboratories.

52 Claims, 5 Drawing Sheets

(52) U.S. Cl.
CPC ....... *G01N 15/1459* (2013.01); *G01N 15/1463* (2013.01); *G01N 15/1484* (2013.01); *A61M 2205/0244* (2013.01); *A61M 2206/11* (2013.01); *B03C 2201/26* (2013.01); *G01N 2015/149* (2013.01); *Y10T 436/25375* (2015.01)

(56) References Cited

U.S. PATENT DOCUMENTS

| | | | |
|---|---|---|---|
| 5,270,199 | A | 12/1993 | Ezekowitz |
| 5,968,820 | A * | 10/1999 | Zborowski et al. ............ 435/325 |
| 5,985,153 | A * | 11/1999 | Dolan et al. .................... 210/695 |
| 6,241,894 | B1 | 6/2001 | Briggs et al. |
| 6,432,630 | B1 * | 8/2002 | Blankenstein .................... 435/4 |
| 6,541,213 | B1 * | 4/2003 | Weigl et al. ..................... 435/7.1 |
| 6,846,649 | B1 | 1/2005 | Thiel et al. |
| 6,875,855 | B1 * | 4/2005 | Roberts et al. ................ 536/23.7 |
| 7,138,269 | B2 | 11/2006 | Blankenstein |
| 7,276,170 | B2 * | 10/2007 | Oakey et al. ................... 210/767 |
| 7,807,454 | B2 | 10/2010 | Oh et al. |
| 2002/0036141 | A1 * | 3/2002 | Gascoyne et al. ............. 204/547 |
| 2003/0129676 | A1 | 7/2003 | Terstappen et al. |
| 2004/0018611 | A1 * | 1/2004 | Ward et al. .................. 435/287.2 |
| 2004/0229212 | A1 | 11/2004 | Thiel et al. |
| 2005/0059041 | A1 * | 3/2005 | Johnson et al. ..................... 435/6 |
| 2005/0061962 | A1 | 3/2005 | Mueth et al. |
| 2005/0121604 | A1 * | 6/2005 | Mueth et al. ................... 250/251 |
| 2005/0274650 | A1 * | 12/2005 | Frazier et al. .................... 209/39 |
| 2006/0223178 | A1 | 10/2006 | Barber et al. |
| 2009/0047297 | A1 * | 2/2009 | Kim et al. ................... 424/184.1 |
| 2009/0078614 | A1 | 3/2009 | Varghese et al. |
| 2009/0220932 | A1 | 9/2009 | Ingber et al. |
| 2010/0044232 | A1 | 2/2010 | Lin et al. |

FOREIGN PATENT DOCUMENTS

| | | |
|---|---|---|
| WO | 2011090954 A2 | 7/2011 |
| WO | 2012100099 A2 | 7/2012 |
| WO | 2013012924 A2 | 1/2013 |

OTHER PUBLICATIONS

Chang et al., "Crystallization and Preliminary X-ray Analysis of a Trimeric Form of Human Mannose Binding Protein", J. Mol. Biol., 1994, 5: 241(1): 125-127.
Chang et al., "Evaporation-induced particle microseparations inside droplets floating on a chip", Langmuir. Feb. 14, 2006;22(4):1459-68.
Courbin et al., "Imbibition by polygonal spreading on microdecorated surfaces", Nature Materials, 2007, 6: 661-664.
Inglis et al., "Continuous Microfluidic Immunomagnetic Cell Separation", Applied Physics Letters, 85(21):5093-5095 (2004).
Jung et al., "Perfluorinated Polymer Monolayers on Porous Silica for Materials with Super Liquid Repellent Properties", Langmuir, 2002, 18 (16), pp. 6133-6139.
Kim et al., "Structural Transformation by Electrodeposition on Patterned Substrates (STEPS): A New Versatile Nanofabrication Method", Nano Letters, 2011, 527-533.
Mach et al., "Continuous scalable blood filtration device using inertial microfluidics", Biotechnol Bioeng, 107(2):302-11 (2010).
Porter et al., "An evaluation of lectin-mediated magnetic bead cell sorting for the targeted separation of enteric bacteria", Bone Marrow Transplant, 84(5):722-32 (1998).
Rowley et al., "Isolation of CD34+ cells from blood stem cell components using the Bacter Isolex system", Bone Marrow Transplant, 21:1253-62 (1998).
Sung et al., "Prevention of air bubble formation in a microfluidic perfusion cell culture system using a microscale bubble trap", Biomed Microdevices. Aug. 2009;11(4):731-8.
Wenzel, "Resistance of Solid Surfaces to Wetting by Water", Ind. Eng. Chem. 1936, 28: 988-994.
Wong et al., Nature, 2011, 477: 443-447. "Bioinspired self-repairing slippery surfaces with pressure-stable omniphobicity."
Xia et al., "Combined microfluidic micromagnetic separation of living cells in continuous flow", Biomed Microdevices, 8 (4):299-308, (2006).
Yung et al., "Micromagnetic-microfluidic blood cleansing device", Lab on a Chip, 9:1171-1177 (2009).

* cited by examiner

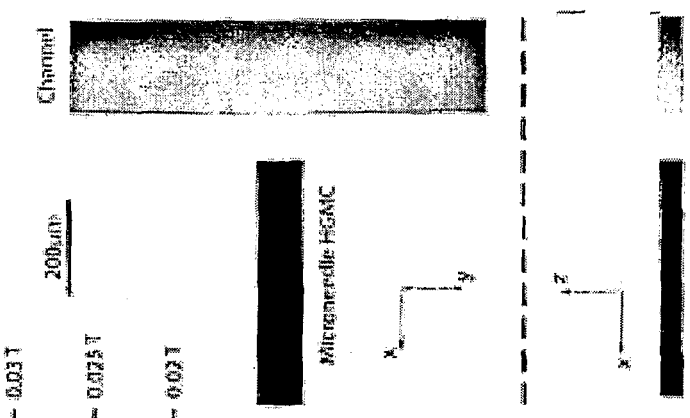
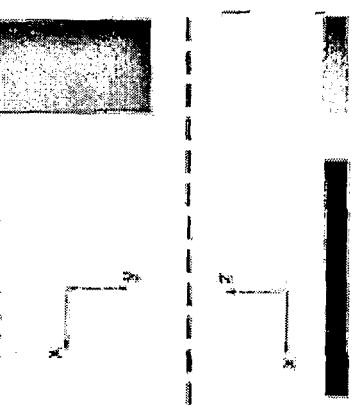
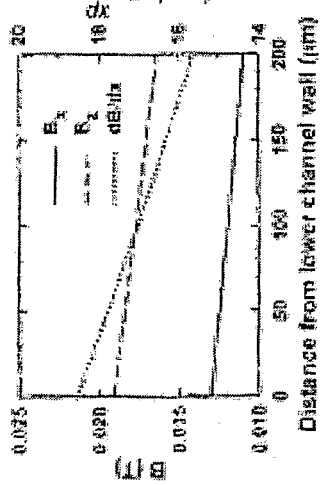
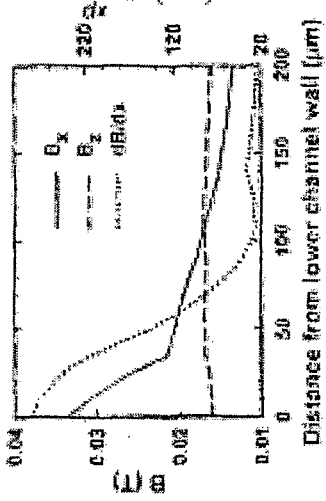
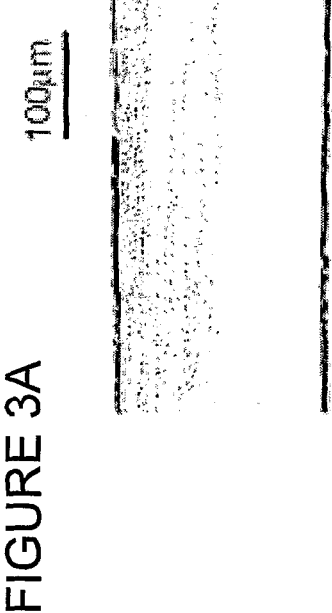
FIGURE 3A
FIGURE 3B
FIGURE 3C
FIGURE 3D
FIGURE 3E ically rare to their large dimensions. With the devel-
DEVICE AND METHOD FOR COMBINED MICROFLUIDIC-MICROMAGNETIC SEPARATION OF MATERIAL IN CONTINUOUS FLOW

CROSS-REFERENCE TO RELATED APPLICATIONS

This application is a 371 National Stage of International Application No. PCT/US2006/039344 filed on Oct. 6, 2006, which designates the United States, and which claims the benefit under 35 U.S.C. §119(e) of U.S. Provisional Application No. 60/724,117 filed on Oct. 6, 2005, the entire contents of which are incorporated herein by reference.

FIELD OF THE INVENTION

The present invention relates to systems and methods for separating materials from biological fluids. More particularly, it relates to devices and methods for quickly and efficiently separating cells or molecules from biological fluids in a microfluidic channel using a high-gradient magnetic concentrator.

BACKGROUND OF THE INVENTION

One of the key functions required for microsystems technologies used for biomedical applications is to separate specific cells or molecules from complex biological mixtures, such as blood, urine, or cerebrospinal fluid. For example, hemofiltration and hemadsorption techniques remove impurities or pathogens in blood. Various physical properties, including size (Huang et al., 2004; Yamada et al., 2004), motility (Cho et al., 2003), electric charge (Lu et al., 2004), electric dipole moment (Fiedler et al., 1998; Hunt et al., 2004), and optical qualities (Fu et al., 1999; Wang et al., 2005), have been studied to separate specific cells or molecules from these mixtures. Magnetic susceptibility also has been explored (Pamme, 2006) because magnetic sorting can be carried out at high-throughput in numerous biological fluids with minimal power requirements, and without damaging the sorted entities (Franzreb et al., 2006; Hirschbein et al., 1982; Lee et al., 2004; Safarik and Safarikova, 1999; Setchell, 1985). Biocompatible superparamagnetic particles are also now available with surfaces modified to promote binding to various molecules and cells. In fact, various macroscale magnetic sorting systems have been built and employed for research and clinical applications (Chalmers et al., 1998; Fuh and Chen, 1998; Handgretinger et al., 1998; Hartig et al., 1995; Melville et al., 1975a; Takayasu et al., 2000) (e.g., to isolate stem cells from batches of pooled blood for bone marrow reconstitution procedures in cancer patients (Handgretinger et al., 1998)).

Batch-type magnetic separators have been microfabricated on single chips that trap magnetic particles in flowing fluids using an external magnetic field, and then the particles are later eluted from the system (Ahn et al., 1996; Deng et al., 2002; Smistrup et al., 2005; Tibbe et al., 2002). However, the loading capacity of these devices is limited because accumulation of the collected particles can restrict fluid flow or lead to irreversible entrapment of samples, and the use of these systems is hampered by the need to disrupt continuous operation for sample elution.

Further, continuous on-chip separation may simplify microsystem operation and potentially improve separation efficiency. In particular, microfluidic systems that are extensively utilized in micro-total analysis systems (µTAS) offer the potential to separate components continuously from flowing liquids. Continuous separation of magnetic particles in microfluidic channels has been demonstrated by manually placing a permanent magnet or electromagnet beside a microchannel that contains multiple outlets (Blankenstein, 1997; Kim and Park, 2005; Pamme and Manz, 2004). However, because each magnet needs to be individually fabricated and positioned, further miniaturization and multiplexing is not possible with this approach.

Additionally, high-gradient magnetic concentrators (HGMCs) can generate a large magnetic force with simple device structures. Macroscale HGMCs have been used in magnetic separations for biomedical applications (Chalmers et al., 1998; Fuh and Chen, 1998; Hartig et al., 1995; Melville et al., 1975a; Takayasu, 2000), but are impractical for microsystems technologies due to their large dimensions. With the development of microfabrication technologies, it has become possible to microfabricate HGMCs along with microfluidic channels on a single chip. Several on-chip HGMC-microfluidic designs for continuous magnetic separation have been reported (Berger et al., 2001; Han and Frazier, 2004, 2006; Inglis et al., 2004). One design used microfabricated magnetic stripes aligned on the bottom of the fluid chamber to horizontally separate magnetically tagged leukocytes trapped on the magnetic stripes away from red blood cells (RBCs) flowing through the chamber (Inglis et al., 2004). In another design, a microfabricated magnetic wire was placed in the middle of the flow stream along the length of a single microfluidic channel, and used to separate deoxyhemoglobin RBCs from white blood cells based on the difference in their relative magnetic susceptibilities (Han and Frazier, 2006).

However, none of these designs provides for portable devices for in-field diagnosis or treatment of diseases caused by blood-borne pathogens, such as sepsis—the body's systemic response to infection in the blood. The overall death rate from this blood infection is 25% in the United States and higher internationally, and in the military field of operation. In a septic patient, the blood becomes overloaded with a rapidly growing infectious agent, and other clearance mechanisms are overcome. The prior attempts have fallen short in that no device presently exists that can rapidly clear infectious pathogens from blood and biological fluids without causing significant blood loss, obstructing blood flow, otherwise altering blood content, or compromising normal organ function.

Thus, there is a need for a device that can rapidly cleanse the blood of pathogens and other biological particulate materials without removing critical normal blood cells, proteins, fluids, or electrolytes. Also, there is a need for biocompatible magnetic labeling particles that will selectively bind to living pathogens within flowing blood such as natural opsonins, while being small enough so that they will not produce vascular occlusion. Moreover, there is a need for a microfluidic separator generating appropriate magnetic field gradients in a microfluidic device for continuous separation of materials from biological fluids in biomedical and biophysical diagnosis and treatment applications.

SUMMARY OF THE INVENTION

The present invention provides technologies for magnetic separation of living cells from biological fluids such as blood, cerebrospinal fluid, urine, and the like. The present invention can be used in portable devices for in-field diagnosis or therapy of diseases caused by blood-borne and other pathogens, such as sepsis and the like. The device and method of the present invention may be employed as on-chip magnetic separation and be used for isolating rare cells, such as cancer cells, stem cells, or fetal cells in the maternal circulation, and the like. The present invention incorporates nanoscale magnetic particles into biological fluids in continuous flow. The biocompatible magnetic nanoparticles bind pathogenic or other cells in the fluid and may be cleared from the fluid by applying an in-line high gradient magnetic concentrator (HGMC) to move magnetically susceptible material across a laminar streamline boundary into a collection stream flow path. The present invention provides an on-chip HGMC-microfluidic system and device that offers improvements over existing designs in terms of biocompatibility, separation efficiency, and rate of clearance, while minimizing the disturbance on normal blood cells and biomolecules. The microfabricated on-chip HGMC-microfluidic system of the present invention efficiently separates magnetic micro- and nano-particles, either alone or bound to living cells, under continuous fluid flow.

BRIEF DESCRIPTION OF THE DRAWINGS

The accompanying drawings illustrate an embodiment of the invention and depict the above-mentioned and other features of this invention and the manner of attaining them. In the drawings:

FIGS. 3A-3E illustrate bright field microscopic images comparing the flow pattern of magnetic beads in a microfluidic channel in the absence and presence of a microfabricated high gradient magnetic field concentrator and graphical depictions of the corresponding magnetic field, magnetic field gradient, and magnetic field distribution pattern in accordance with the present invention.

DETAILED DESCRIPTION OF THE INVENTION

The following detailed description of the invention refers to the accompanying drawings and to certain embodiments, but the detailed description of the invention does not limit the invention. The scope of the invention is defined by the appended claims and equivalents as it will be apparent to those of skill in the art that various features, variations, and modifications can be included or excluded based upon the requirements of a particular use.

The present invention extends the functionality of current microfluidic systems techniques to provide on-chip technologies for magnetic separation of living cells from biological fluids such as blood, cerebrospinal fluid, urine, and the like. The present invention combines magnetic and microfluidic separation technologies in continuous flow applications thereby creating effectively unlimited binding and clearance capacity that can be used in portable devices for in-field diagnosis or therapy of diseases, for example, diseases caused by blood-borne pathogens, such as sepsis and the like. The system and method of the present invention has many advantages over prior systems since the micromagnetic-microfluidic separation techniques of the present invention may be multiplexed to offer high throughput field diagnosis and treatment options. The separation technologies may also be used in an on-chip environment for isolating rare cells, such as cancer cells, stem cells, and the like. Further, the present invention offers improvements over existing designs in terms of biocompatibility, separation efficiency, and rate of clearance, while minimizing the disturbance on normal blood cells and biomolecules. The microfabricated on-chip high gradient magnetic field concentrator (HGMC)-microfluidic system of the present invention efficiently separates magnetic micro- and nano-particles, either alone or bound to living cells, such as bacteria, under continuous fluid flow.

Separation Microsystem Overview

Figure 1:
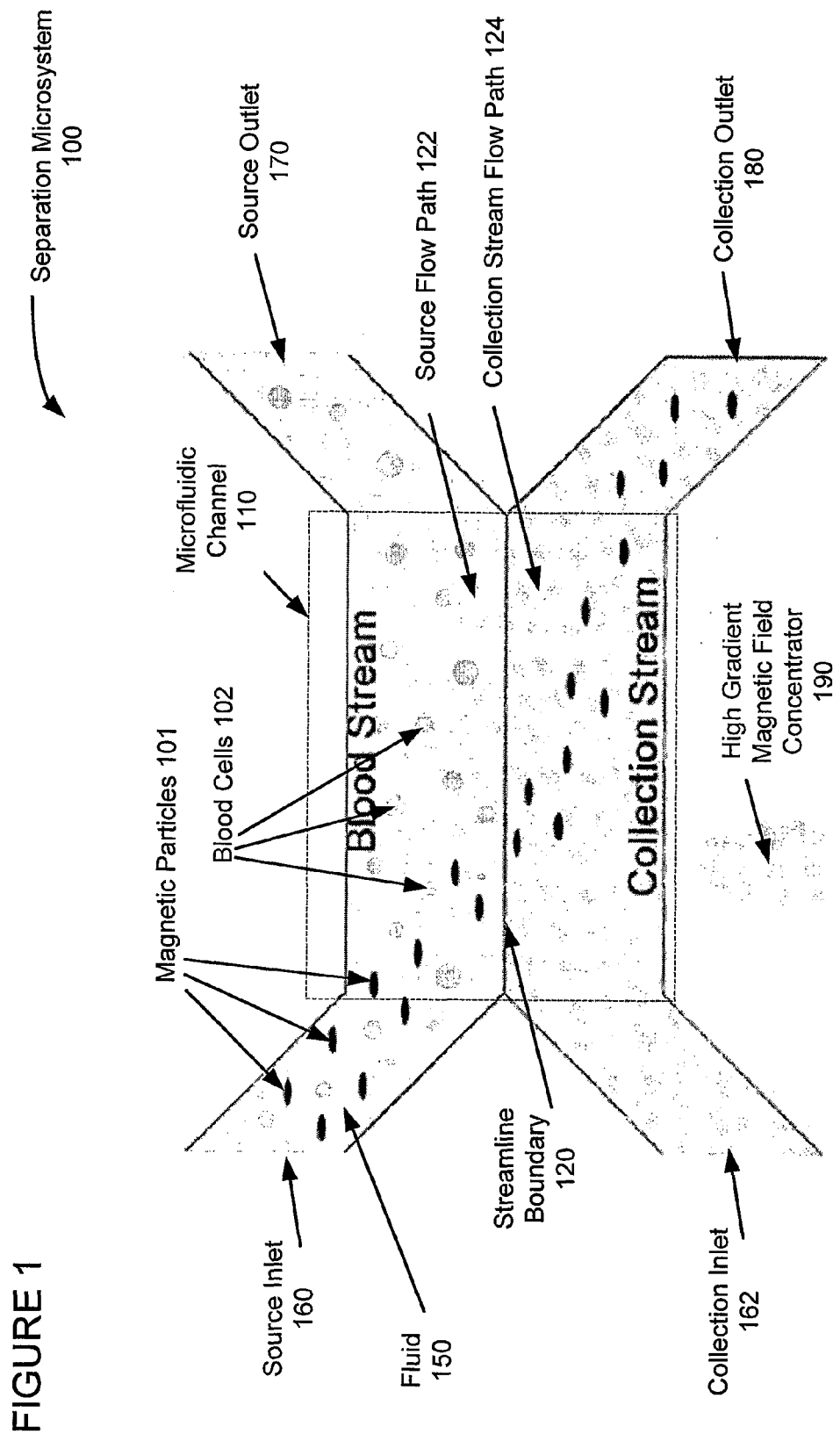
FIG. 1 shows a schematic illustration of an on-chip HGMC-microfluidic separator in accordance with an embodiment of the present invention.

As shown schematically in FIG. 1, an embodiment of the separation microsystem 100 of the present invention incorporates magnetic particles 101 that may be injected into the fluid 150. Magnetic particles 101 bind to material (not shown separately) in the fluid 150. Fluid 150 enters microfluidic channel 110 through source inlet 160 and flows through microfluidic channel 110. Microfluidic channel 110 includes at least one dimension less than 1 mm and exhibits laminar flow. The fluid 150 may flow in discrete volumes or may flow continuously to increase efficiency in the separation techniques of the present invention.

Microfluidic channel 110 includes a streamline boundary 120 that effectively separates the source flow path 122 from the collection stream flow path 124 in the microfluidic channel 110. A high gradient magnetic field concentrator 190 is magnetized to move the material bound to magnetic particles 101 to cross the streamline boundary 120 and enter the collection stream flow path 124 to effectively and efficiently separate the material bound to magnetic particles 101 from the fluid 150 in the microfluidic channel 110.

As fluid 150 flows in the microfluidic channel 110, the material bound to magnetic particles 101 and affected by the high gradient magnetic field concentrator 190 flows in the collection stream flow path 124 to a collection outlet 180. The fluid 150 and any other material not affected by the magnetized high gradient magnetic field concentrator 190 does not cross the streamline boundary 120 and thereby remains in the source flow path 122. As fluid 150 flows in the microfluidic channel 110, material unaffected by the magnetized high gradient magnetic field concentrator 190 continues to flow in the source flow path 122 and exits the microfluidic channel 110 through source outlet 170. Separation microsystem 100 can be used to continuously transfer material labeled with magnetic particles 101 out of the source flow path 122 to a collection outlet 180 to provide high throughput cleansing of fluid 150.

Separation Microsystem Fabrication

In another embodiment, the microfluidic channel 110 may be prepared by soft lithography (McDonald and Whitesides, 2002) and have dimensions of 20×0.2×0.05 mm (L×W×H), for example. A negative mold of the microfluidic channel 110 may be produced in SU-8 photoresist (Microchem, Inc.). Poly(dimethylsiloxane) (PDMS) (Slygard 184, Dow Corning) may be poured onto the mold, allowed to cure for 1 hour at 65° C., and peeled off to form the microfluidic channel 110. A lift-off process (Wolf, 1986) may be used to microfabricate the high gradient magnetic field concentrator 190 by defining a base layer of evaporated metal (Ti/Au, 10 nm/50 nm) in the form of a microneedle (20 mm in X, 100 μm in Y, 50 μm in Z) or a microcomb (3.8 mm in X, 12 mm in Y, 50 μm in Z with teeth 300 μm in X and spaced by 200 μm in Y), or a magnetic line array, for example, on a glass substrate that may then be electroplated (1 mA for 4 hr) with a 50 μm thick layer of magnetic material (80% Ni, 20% Fe) (Rasmussen et al., 2001). The geometry of the high gradient magnetic field concentrator 190 is used to produce a steep, uniform magnetic field gradient across the width of the microfluidic channel 110. Electrodeposition and photolithography may be used to fabricate a high gradient magnetic field concentrator of magnetic material such as NiFe or the like. In one embodiment of the present invention, a microfluidic channel was fabricated containing a 12 mm long layer of NiFe placed along a side edge of the microfluidic channel as a soft magnetic high gradient magnetic field concentrator. The PDMS microfluidic channel 110 and the glass substrate with the NiFe layer may then be exposed to oxygen plasma (100 W, 60 sec) and bonded together to form a separation microsystem 100 of the present invention.

A soft magnetic material, such as NiFe, for example, with low remnant magnetization was magnetized with an external stationary magnet to facilitate rapid and switchable control of cell separations. The system of the present invention may also be microfabricated using permanent magnetic materials or incorporate elements that provide electromagnetic control. Moreover, the same microfabrication techniques could be used to deposit multiple magnetic layers at different positions on one chip simultaneously, thus providing multiplexing capabilities in accordance with the present invention.

Magnetic Particles (Beads and Cells) Used to Label Target Material

In one embodiment of the present invention, non-magnetic red-fluorescent beads (2 μm diameter, $4.5 \times 10^9$ beads/ml, Molecular Probes) and superparamagnetic green-fluorescent beads (1.6 μm, 43% iron oxide, $3.1 \times 10^9$ beads/ml, Bangs Laboratories) were incubated in 10× volume of 1% albumin solution for 1 hour before being combined and injected into the microfluidic channel 110. *E. coli* (HB101 K-12) bacteria expressing green fluorescent protein (GFP) were grown overnight at 37° C. in LB medium containing ampicillin (100 μg/ml) and arabinose (0.1%, inductor of GFP expression), then harvested and resuspended in PBS buffer. The *E. coli* ($1 \times 10^9$ CFU/ml) were labeled with biotinylated anti-*E. coli* antibody (Virostat; mixing ratio 2 μg antibody/$10^7$ cells), and mixed with streptavidin-coated superparamagnetic particles (130 nm, 85% iron oxide, G. Kisker GbR) prior to addition to the microfluidic separation system 100. Human RBCs (75% hematocrit) were obtained from the blood bank at Children's Hospital Boston, stained with the red fluorescent dye (SYTO 64, Molecular Probes), and mixed with isotonic saline containing 0.5% albumin at a 1:3 ratio (final density around $2 \times 10^9$ RBCs/ml).

Microfluidic Control Testing

Fluidic connections, such as source inlet 160, source outlet 170, collection inlet 162, and collection outlet 180, to the microfluidic channel 110 were made with polyethylene tubing inserted through holes punched through the PDMS. Syringe pumps were used to control the flow rate at each of the inlets 160, 162 independently. Prior to each test, the microfluidic channel 110 and tubing were cleaned by flushing with 70% ethanol, rinsing with deionized water, and incubating in phosphate buffered saline (PBS) with 1% albumin for 30 min. The fluid 150 containing the sample target material and a dextran solution (32%, 70 kDa) were injected simultaneously into the source and collection inlets 160, 162, respectively. All tests were carried out using experimental samples contained within the first half of the volume from syringes in the upright position. Separations of target materials and the magnetic particles in the microfluidic channel 110 were monitored in real-time using an inverted Nikon TE2000-E microscope equipped with a CCD camera, and optimized by adjusting the fluid flow rate and the output split ratio. The width of the source flow path was maintained as ⅓-½ of the microfluidic channel width.

While some cell separation techniques such as fluorescence-activated cell sorting (FACS) have achieved a sorting rate of approximately 100 cells/s (Wang et al., 2005), because FACS and similar systems are serial processes allowing only one cell to pass through the actuator at a time, further increases in sample throughput require improvement in the cycle time of the actuator. In contrast, the throughput of the micromagnetic separator of the present invention increases when the cell density of the sample is raised, and a cell throughput of 10,000 cells/s is demonstrated. This enhanced throughput is possible because the wide source path used here (⅓-½ of channel width) allows large numbers of beads and cells to pass through the separating magnetic field gradient simultaneously. Thus, the system and device of the present invention is especially useful for separations from blood or other clinical samples with high cell density and low optical transparency.

In addition to increasing the width of the channel flow path, a disk-shaped (4 mm diameter, 2 mm high, magnetized along the z-axis) neodymium permanent magnet was used to magnetize the NiFe layer high gradient magnetic field concentrator 190. Of course, any suitable magnet source may be used to magnetize the gradient magnetic field concentrator 190, including for example, permanent magnets, electromagnets, paramagnetic sources, and the like. Likewise, the magnetic source may be inherent to the high gradient magnetic field concentrator, such as when the high gradient magnetic field concentrator includes permanent magnetic materials that do not require an external magnetizing field. In one embodiment of the present invention, the neodymium permanent magnet was positioned in the middle of the NiFe layer in the flow direction with its center 4 to 5 mm from the closest side of the microfluidic channel 110 using a microscope micromanipulator. A schematic configuration of the separation microsystem 200 is shown also in FIG. 2A and FIG. 2B with a detailed view of the microfluidic channel.

Quantification of Separation Efficiencies

Quantification of clearance efficiency using the fluorescent microbeads may be performed using the inverted Nikon TE2000-E microscope or any similar examination device by measuring the fluorescence intensity of the collected fluids from both outlets 170, 180. In one embodiment of the present invention using *E. coli*, the high density of bound magnetic nanoparticles blocked the green fluorescent protein (GFP) signal. Thus, collected bacterial numbers may be quantified by transferring the fluids collected from the outlets 170, 180 to a growth medium and culturing at 37° C. The optical density of the cell solutions at 600 nm ($OD_{600\ nm}$) may be measured periodically. Cell numbers may be determined using $OD_{600\ nm}$ obtained during the logarithmic phase of growth, and $OD_{600\ nm}$ during this phase was linearly related to the starting concentration of the magnetically-labeled *E. coli* bacteria.

Operation of the Separation Microsystem

Figures 2A, 2B:
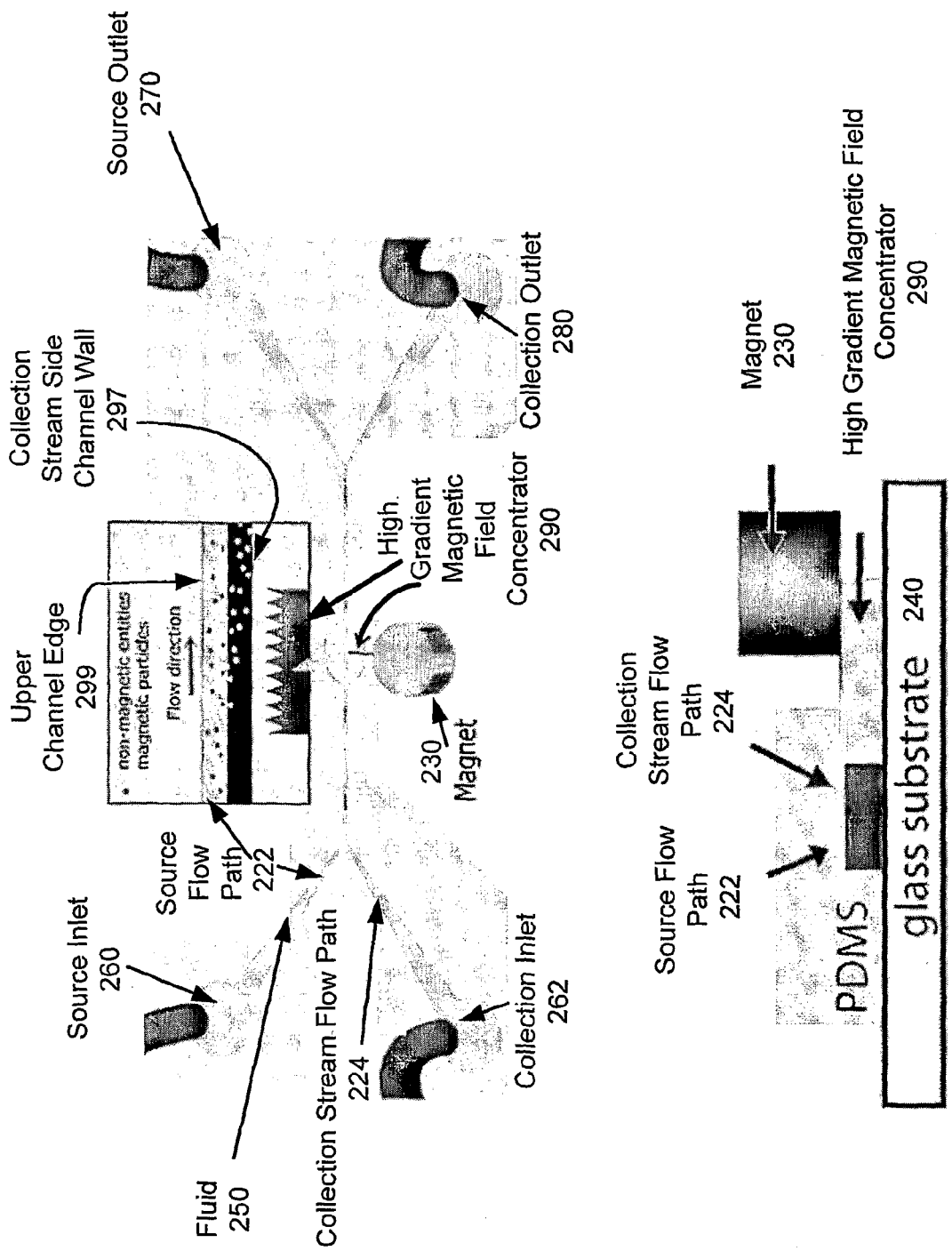
FIGS. 2A-2B show a schematic illustration of an on-chip HGMC-microfluidic separator with a detailed view of the microfluidic channel in accordance with an embodiment of the present invention.

FIG. 2A shows a three dimensional schematic view of an on-chip HGMC-microfluidic separator 200 with a detailed inset view of the microfluidic channel in accordance with an embodiment of the present invention. The microfabricated on-chip microfluidic-micromagnetic cell separator of the present invention may be used to continuously cleanse contaminant materials such as bacteria, particulates, and the like from biological fluids. FIG. 2B illustrates a cross sectional view of the microfluidic separator. Where possible in FIG. 2A and FIG. 2B, like reference numerals have been used to designate like features that are common to FIG. 1.

As shown schematically in FIG. 2A, the combined micro-magnetic-microfluidic separation system 200 contains a high gradient magnetic concentrator 290 adjacent to the microfluidic channel 210. The high gradient magnetic concentrator 290 may contain a microfabricated layer of soft magnetic material, such as NiFe, or other suitable magnetic materials. The single microfluidic channel 210 is connected to two inlets 260, 262 and two outlets 270, 280. Due to the small Reynolds number (Re) of microfluidic channels, the flow of fluid 250 remains laminar with mixing due only to diffusion across the source flow path 222 and the collection stream flow path 224. In one embodiment of the present invention, a layer of magnetic material such as NiFe with the same thickness as the height of the microfluidic channel 210 may be deposited adjacent to the channel 210 during the microfabrication process to create an on-chip high gradient magnetic concentrator 290 (HGMC) with defined geometry such as a microneedle, microcomb, magnetic line array, and the like.

The thickness of the high gradient magnetic concentrator 290 corresponds to the height of the microfluidic channel 210 to ensure that the magnetic particles 201 and target materials flowing at different heights through the microfluidic channel 210 were exposed to similar magnetic field gradients. While channel height does not affect the separation efficiency of the system of the present invention, it influences the volume flow rate. In one embodiment of the present invention, a relatively small channel height (50 μm) was chosen to facilitate real-time focusing and monitoring of flows in the channel under microscopic visualization. Higher volume throughput may be achieved by increasing the channel height and the magnetic layer thickness in parallel. As an example, a fluidic channel that is centimeters long with a source flow path and a collection stream flow path each 100 microns wide may be employed, but instead of a channel height of 50 microns, the channel height may be centimeters high. The sorting rate will scale upward with the height of the channel.

When magnetized by an external magnet, the HGMC 290 locally concentrates the gradient of the applied magnetic field to move the magnetic particles 101 that are present in the source flow path 222 (shown in detail as upper path 222 in the FIG. 2A inset) across the laminar flow streamline boundary 220 and into the neighboring collection stream flow path 224 (also shown in detail as lower path 224 in the FIG. 2A inset). The external magnet may be any suitable magnet, such as a permanent magnet, an electromagnet, or the like. In one embodiment of the present invention, an external permanent neodymium magnet was used to magnetize the HGMC 290 of the present invention.

FIG. 2A inset further illustrates how magnetic particles 201, such as magnetic beads, flowing in the upper source flow path 222 are pulled across the laminar streamline boundary 220 into the lower collection stream flow path 224 when subjected to a magnetic field gradient produced by the microfabricated NiFe layer located along the lower side of the microfluidic channel 210. Also shown in the FIG. 2A inset, fluid flow is illustrated in the y-direction, the magnetic field gradient across the channel is in the x-direction, and the channel height is in the z-direction.

The affected particles 201 will then exit through the lower collection outlet 280. Under the same conditions, non-magnetic particles 202 in the source flow path are unaffected by the applied magnetic field gradient, and thus, they will exit the microfluidic channel 210 through the upper source outlet 270.

FIG. 3A and FIG. 3B were constructed by overlaying sequential frames of time-lapse movies recorded at the middle of the microfluidic channel of the present invention. FIG. 3A illustrates the flow pattern of magnetic beads in the absence of a high gradient magnetic field concentrator, while FIG. 3B shows the flow pattern of magnetic beads in the presence of a high gradient magnetic field concentrator in accordance with the present invention.

As shown in FIG. 3A, in one embodiment of the present invention, a volume flow rate of 5 μl/hr (0.3 mm/s) was established through the microfluidic channel. At this flow rate, the microfabricated separation device containing a magnetized NiFe high gradient magnetic field concentrator 290 in the form of a microneedle oriented perpendicularly to the flow paths 222, 224 and juxtaposed to the side of the microfluidic channel 210 drove the magnetic particles 201 (magnetic beads with 1.6 μm diameter) flowing in the upper source flow path 222 to cross over the streamline boundary 220 and enter the lower collection stream flow path 224 as depicted in FIG. 3B. The magnetic particles 201 eventually exited the microfluidic channel 210 through the collection outlet 280. This separation was possible because the NiFe high gradient magnetic field concentrator 290 microneedle generated a stronger magnetic field gradient across the channel (i.e., greater than 25 T/m), with a field strength in the vertical and horizontal directions of greater than 0.016 and greater than 0.013 T, respectively, when magnetized by the magnetic source of the external neodymium magnet. Additional magnetic sources such as paramagnetic sources, electromagnets, and the like, may also be used to magnetize the high gradient magnetic field concentrator 290. Additionally, the magnetic source may be inherent to the high gradient magnetic field concentrator, such as when the high gradient magnetic field concentrator includes permanent magnetic materials that do not require an external magnetizing source. The results of the magnetization using the neodymium magnet are shown in FIG. 3D and FIG. 3E, and are described further in the Appendix. The corresponding magnetic field is illustrated as a function of distance from the collection stream flow path channel wall 297 in FIG. 3C, and in FIG. 3D, the magnetic field gradient is presented as a function of distance from the collection stream flow path channel wall 297. The solid, dashed, and dotted lines in the graphs of FIG. 3C and FIG. 3D correspond to the vertical magnetic field ($B_z$), horizontal magnetic field ($B_x$) and the magnetic field gradient across the channel $$\left(\frac{d\vec{B}}{dx} \cdot \hat{B}\right),$$

respectively. In FIG. 3E, computer-simulated magnetic field distributions are depicted as grayscale variations within the microfluidic channel generated by the magnetized high gradient magnetic field concentrator 290 in the form of a NiFe microneedle. Both top (top FIG. 3E) and cross-sectional (bottom FIG. 3E) views are illustrated.

Additionally, to increase throughput, volume flow rates may be increased to 25 μl/hr. With increased volume flow rates, stronger magnetic field gradients need to be produced by the high gradient magnetic field concentrator 290 to maintain the separation efficiency of the microfluidic separation device 200.

Figure 4C:
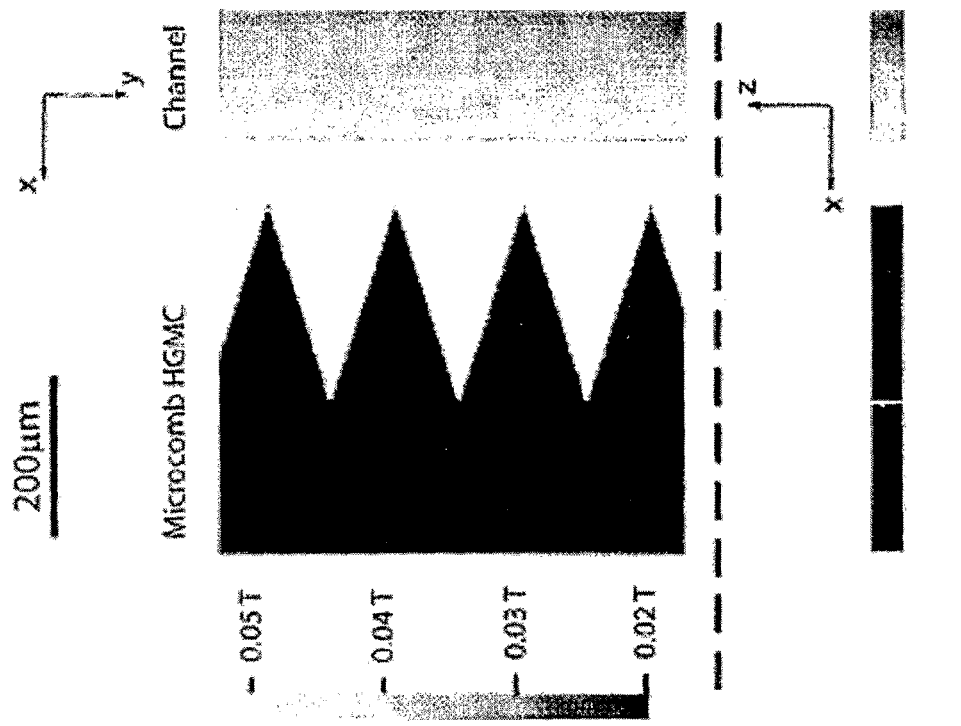
FIGS. 4A-4C illustrate a microscopic view of a high gradient magnetic field concentrator, the corresponding magnetic field and magnetic field gradient, and a simulated magnetic field distribution in accordance with an embodiment of the present invention.
Figure 4A:
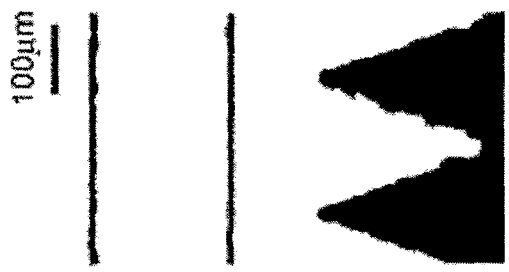
Figure 4B:
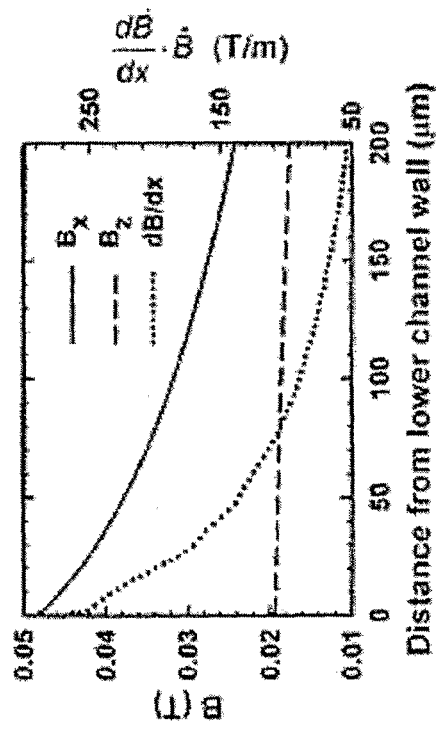

For example, to increase the separation efficiency of the on-chip HGMC-microfluidic separator, one embodiment of the present invention employs a microfabricated NiFe layer in a microcomb configuration that has a triangular saw-tooth edge as shown in FIG. 4A. In operation, the triangular sawtooth edged high gradient magnetic field concentrator is positioned close to the side of the microfluidic channel. Due to its high curvature geometry, the microcomb high gradient magnetic field concentrator concentrates the magnetic field and produces a steep magnetic field gradient across the width of the microfluidic channel 210 without providing excessive trapping of particles 201 near the channel wall. The saw-tooth edge of the microcomb provides horizontal and vertical magnetic fields of 0.025 T and 0.018 T, respectively, at the far edge of the channel, and a field gradient of 50 T/m as shown in FIG. 4B and FIG. 4C and described further in the Appendix. Additional successful tests were performed with a magnetic field gradient over a range of 1 to 500 T/m, with preferred results in the range of 15 to 150 T/m. In addition, the region of the microfluidic channel exposed to the magnetic field gradient along its length (in the y-direction) was increased to 12 mm as described above.

In FIG. 4B, the magnetic field and the magnetic field gradient are presented as a function of distance from the collection stream flow path channel wall 297. The solid, dashed, and dotted lines in the graphs of FIG. 4B correspond to the vertical magnetic field ($B_z$), horizontal magnetic field ($B_x$) and the magnetic field gradient across the channel $$\left(\frac{d\vec{B}}{dx} \cdot \hat{B}\right),$$

respectively. In FIG. 4C, computer-simulated magnetic field distributions are depicted as grayscale variations within the microfluidic channel generated by the magnetized high gradient magnetic field concentrator 290 in the form of a NiFe microcomb. Both top (top FIG. 4C) and cross-sectional (bottom FIG. 4C) views are illustrated.

Figure 5A:
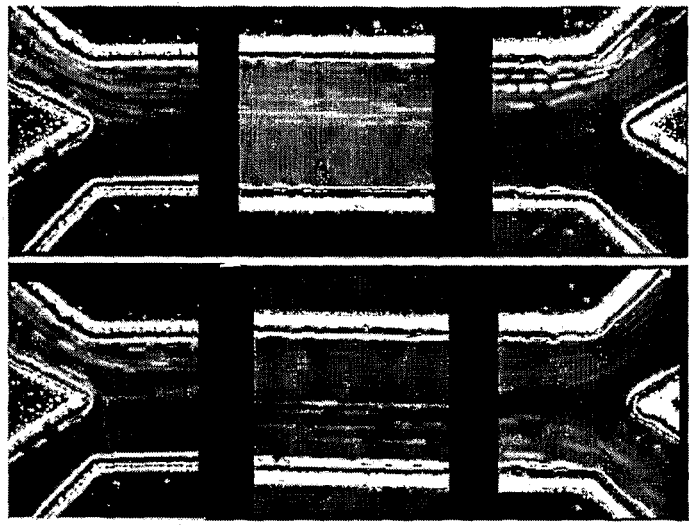
FIGS. 5A-5C illustrate magnetic separations of magnetic and non-magnetic beads cells using a combined microfluidic-micromagnetic separator in accordance with the present invention.
Figure 5B:
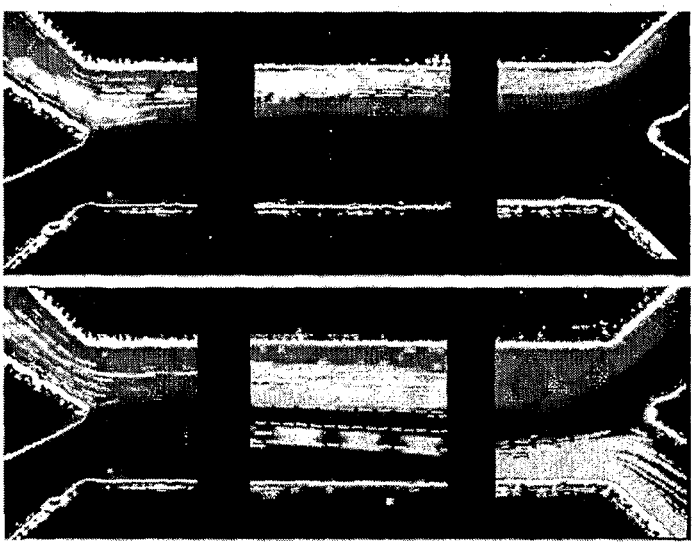
Figure 5C:
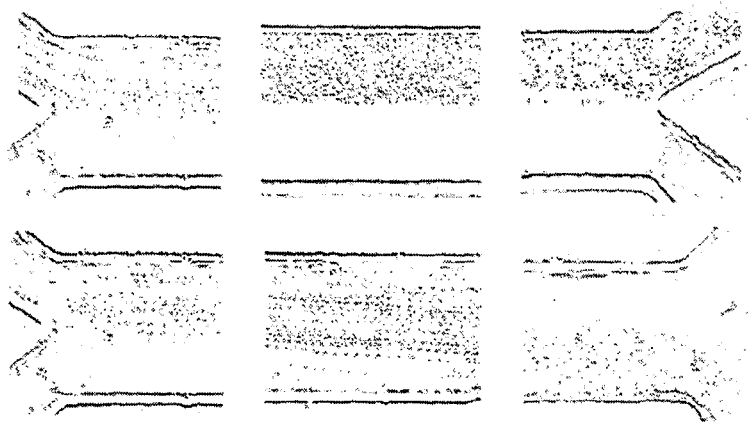

To quantify the separation efficiency and to further analyze the performance of the micromagnetic separator device with the NiFe microcomb high gradient magnetic field concentrator for magnetic particle separation, green fluorescent magnetic beads (1.6 μm diameter; $1.6 \times 10^7$ beads/ml) were mixed with red fluorescent non-magnetic beads (2 μm diameter; $2.2 \times 10^7$ beads/ml) in PBS and introduced into the source path as shown in FIG. 5A (top). FIGS. 5A-C were generated by overlaying sequential frames of corresponding movies taken at the beginning, middle, and end (left to right) of the microfluidic channel, in the absence (top) or presence (bottom) of each pair of images.

Without magnetization, both the magnetic and non-magnetic beads followed their laminar source flow path and thus, both the red and green microbeads exited from the top source outlet as shown in FIG. 5A (top). When the NiFe high gradient magnetic field concentrator microcomb was magnetized, almost all of the green magnetic beads observed under the microscope were pulled from the source flow path 222 across the laminar streamline boundary 220 and into the collection stream flow path 224 and exited through the lower collection outlet 280, whereas the red non-magnetic beads remained in the original upper source flow path as shown in FIG. 5A (bottom).

As shown in Table 1 below, quantification of the separation efficiency of the magnetic beads at the collection outlet revealed that, at a volume flow rate of 40 μl/hr, 92% of the magnetic beads exited from the collection outlet, whereas less than 1% of the non-magnetic beads were present in this fraction. The same green magnetic beads ($1.6 \times 10^7$ beads/ml) were then mixed in isotonic saline with red dye (Syto 64)-stained human RBCs at a concentration similar to that in blood ($2 \times 10^9$ cells/ml), and injected into the top source inlet of the microfluidic channel as shown in FIG. 5B (top). Again, the device of the present invention efficiently separated the magnetic beads from the flowing RBCs using the on-chip HGMC-microfluidic separator. These results are shown in FIG. 5B (bottom versus top). Also shown in Table 1, at a flow rate of 25 μl/hr, 83% of the magnetic beads and less than 1% of RBCs were retrieved from the collection outlet. This also confirmed that the effect of the magnetic force generated by the magnetized NiFe layer on RBCs is insignificant in this system.

With further regard to Table 1, the "flow rate" column is indicative of the flow rate of the source flow path in the microfluidic channel. At least 10 μl of fluid volume was collected for quantification using the flow rate indicated. "Throughput" of the system was estimated based on the flow rate and the cell or bead density of the sample. The magnetic nanoparticles used for labeling $E.\ coli$ were not included when calculating throughput. The separation efficiencies are depicted in FIGS. 5A-5C and were calculated in two ways. The left column of the separation efficiency entry was calculated using $I_{c,mag}/(I_{c,mag}+I_{s,mag})$. The right column of the separation efficiency entries was calculated using $I_{c\ mag}/(I_{s,non-mag})$, where $I_{c\ mag}$ and $I_{s,mag}$ are the intensity (fluorescence or $OD_{600\ nm}$) of beads or cells collected at the lower outlet and upper outlet, respectively, with magnetic field turned on, and $I_{s,non-mag}$ is the intensity (fluorescence or $OD_{600\ nm}$) of beads or cells collected at the upper source outlet with the magnetic field turned off. Additionally, the amount of non-magnetic beads or RBCs collected at the lower collection outlet was less than 1% of the amount of non-magnetic beads or RBCs collected at the upper source outlet in all tests. With regard to test number 3, for better visualization of the streamline boundary, the PBS buffer contained Texas Red-conjugated bovine serum albumin (0.1 mg/ml). Additionally, with regard to test number 4, the magnetic sample components included $E.\ coli$ ($5 \times 10^6$ cells/ml)+130 nm magnetic particles ($5 \times 10^9$ particles/ml). Similarly, in test 5, the magnetic sample components included $E.\ coli$ ($5 \times 10^6$ cells/ml)+130 nm magnetic particles ($1.0 \times 10^{10}$ particles/ml).

TABLE 1

Results of sorting particles and cells using the combined microfluidic-micromagnetic separator with the NiFe microcomb

| Test | Sample components | | Flow rate (μl/hr) | Throughput (beads or cells/s) | Separation efficiency (%) | |
| --- | --- | --- | --- | --- | --- | --- |
| | Magnetic | Non-magnetic | | | | |
| 1. | 1.6 μm beads | 2 μm beads in PBS | 40 | 420 | 92 ± 4 | 86 ± 6 |
| 2. | 1.6 μm beads | RBCs in saline | 25 | 10,000 | 83 ± 5 | 79 ± 5 |
| 3. | $E.\ coli$ + 130 nm beads | PBS | 30 | 80 | 89 ± 6 | 83 ± 9 |

TABLE 1-continued

Results of sorting particles and cells using the combined microfluidic-micromagnetic separator with the NiFe microcomb

| Test | Sample components | | Flow rate (µl/hr) | Throughput (beads or cells/s) | Separation efficiency (%) | |
| --- | --- | --- | --- | --- | --- | --- |
| | Magnetic | Non-magnetic | | | | |
| 4. | E. coli + 130 nm beads | RBCs in saline | 25 | 10,000 | 53 ± 8 | 44 ± 11 |
| 5. | E. coli + 130 nm beads | RBCs in saline | 25 | 10,000 | 78 ± 10 | 70 ± 9 |

In one embodiment of the present invention, living *E. coli* bacteria were separated by the microfluidic separation system. The separation techniques were performed using the on-chip HGMC-microfluidic separator on living *E. coli* bacteria in flowing fluids, both alone and when mixed with RBCs. In these studies, 130 nm magnetic particles were used to label *E. coli* bacteria ($1 \times 10^7$ cells/ml) by incubating the cells with biotinylated anti-*E. coli* antibody, mixing them with 130 nm magnetic nanoparticles coated with streptavidin ($1.0 \times 10^{10}$ particles/ml) in PBS, and then injecting them into the source inlet of the microfluidic channel. Nanometer-sized (130 nm) were used to label the bacteria because they bind more efficiently to *E. coli* compared to micrometer-sized magnetic beads with similar surface functionality, likely due to the increased steric hindrance with micrometer-sized beads. Further, magnetic nanoparticles are less likely to occlude small vessels and have longer circulation times than microbeads (Gupta, 2004) and are better suited for the in-line microfluidic separation device for cleansing blood or other biological fluids of biopathogens, such as in septic patients.

Upon activating the magnetic field gradient, almost all of the observed *E. coli* cells originally confined to the upper laminar source flow path as shown in FIG. 5C (top) were moved to the lower collection stream flow path and passed out through the collection outlet as shown in FIG. 5C (bottom). At a flow rate of 30 µl/hr, 89% the *E. coli* cells were separated from the source original flow path. Similar studies confirmed that *E. coli* ($5 \times 10^6$ cells/ml; $0.5 \times 10^{10}$ magnetic nanoparticles/ml) could be separated from saline containing a physiological concentration of RBCs ($2 \times 10^9$ cells/ml), but the separation efficiency of *E. coli* at the collection outlet was 53% at a flow rate of 25 µl/hr. This decreased separation efficiency may be due to the increased viscosity of this fluid which contains RBCs, as opposed to PBS. However, the separation efficiency was greatly improved when the ratio of magnetic nanoparticles to bacteria was increased. For example, as shown in Table 1, at the same flow rate, 78% of the *E. coli* bacteria were retrieved through the collection outlet in a single pass when twice the amount of the magnetic particles were utilized ($5 \times 10^6$ cells/ml; $1.0 \times 10^{10}$ magnetic nanoparticles/ml).

The separation efficiency of the magnetic entities at the collection outlet of the microfabricated on-chip microfluidic-micromagnetic cell separator device ranged from 78% to over 90% at volume flow rates of 25 µl/hr to 40 µl/hr. As listed in Table 1, at low magnetic bead or cell densities on the order of approximately $10^7$ beads or *E. coli*/ml, a throughput of more than 80 beads or cells/s was routinely achieved using the micromagnetic separator device. Moreover, when sorting samples with a high cell density, such as approximately $10^9$ RBCs/ml, for example, the throughput of the microdevice increased to 10,000 cells/s, as also listed in Table 1.

Both *E. coli* and the magnetic nanoparticles have multiple binding sites available on their surfaces, and thus they are potential crosslinkers and upon mixing, can form large clusters composed of multiple *E. coli* bacteria. Such clusters will have a much larger effective diameter than an individual *E. coli* bacterium bound to magnetic particles and hence, they will exhibit a decreased magnetic deviation distance in the x-direction. See Equation (1) in the Appendix. Increasing the ratio of magnetic nanoparticles to bacteria reduces the formation of such clusters. When the ratio of magnetic nanoparticles to bacteria was doubled, the separation efficiency of *E. coli* from the fluids containing a physiological concentration of RBCs increased from 53% to 78%. This increased separation efficiency may be due to the reduction in both the size and number of *E. coli*-magnetic nanoparticle clusters.

Heterogeneity in the size and magnetic properties of magnetic susceptible components in the source mixture results in a wide distribution of magnetic deviation distances in the x-direction during continuous separation (see Appendix). Although this is beneficial for applications such as on-chip magnetophoresis (Pamme and Manz, 2004), for magnetic separations of bacteria or cells from biological fluids, variations in magnetic deviation distance need to be minimized. In the system of the present invention, a viscous dextran solution was used as the collection medium for this purpose, but other viscous solutions such as albumin or lipid solutions, and the like may also be used. See Equation (4) in the Appendix. These viscous solutions serve as the collection media to focus distribution of the magnetically susceptible target material in the collection stream flow path based upon a magnetic deviation distance. That is, the dextran and other viscous solutions provide a collection flow path that serves to focus the target material within an acceptable range of distances where the material may be easily collected via the collection outlet. With a suitable viscous solution, the magnetically susceptible materials will not overshoot the collection stream flow path based on their strong attraction to the high gradient magnetic field concentrator, nor will they undershoot the collection stream flow path due to a collection media that provides too much resistance for the magnetically susceptible particles to overcome. In the system of the present invention, even though occasional sample trapping on the collection side of the channel wall was observed, this effect was small, as indicated by the less than a 10% difference between the separation efficiencies of the magnetic beads and cells calculated with two methods as shown in Table 1 and described above.

In the system of the present invention, the high gradient magnetic field concentrator, such as the NiFe layer, for example, is positioned outside the microfluidic channel to eliminate concerns for the biocompatability of the magnetic materials used. For example, the nickel used in past magnetic separation applications (Han and Frazier, 2004, 2006) may exhibit biocompatibility problems (Takamura et al., 1994; Uo et al., 1999; Wataha et al., 2001). Also, by placing the high gradient magnetic field concentrator at a distance (100 µm) from the channel, magnetic particles are less likely to be trapped by the magnetic field at the channel edge. The magnetic field gradient created is effective at driving movement of magnetic microbeads or *E. coli* labeled with magnetic nanoparticles into the collection stream flow path while not significantly displacing RBCs that may be slightly magnetic because they contain deoxyhemoglobin (Melville et al., 1975b; Takayasu et al., 1982) (see Appendix).

The foregoing description of exemplary aspects and embodiments of the present invention provides illustration and description, but is not intended to be exhaustive or to limit the invention to the precise form disclosed. Those of skill in the art will recognize certain modifications, permutations, additions, and combinations of those embodiments are possible in light of the above teachings or may be acquired from practice of the invention. Therefore, the present invention also covers various modifications and equivalent arrangements that would fall within the purview of appended claims and claims hereafter introduced.

APPENDIX

High Gradient Magnetic Field Concentrator-Microfluidic Design Analysis & Development
Design Analysis The force on a magnetic particle aligned with a magnetic field is given by $\vec{F}_{mag} = m\hat{B} \cdot \nabla \vec{B}$, where m is the magnetic moment of the particle, B is the magnetic field, and $\hat{B}$ is the unit vector in the direction of B. In the microfluidic channel with fluid flow in the y-direction and a perpendicular magnetic field gradient in the x-direction, material such as magnetic particles in the fluid will shift toward the maximum of the magnetic field, cross the streamline bondary, and traverse the microfluidic channel in the x-direction. See FIG. 2 inset. After passing through the magnetic field, the particle's final distance from the source flow side of channel wall, that is the upper channel edge 299 in FIG. 2 inset, $X_{final}$ is approximated by:

$$X_{final} = \frac{\left(m \frac{d\vec{B}}{dx} \cdot \hat{B}\right) L_y}{3\pi \eta D v_y} + X_{initial} \quad (1)$$

Assuming that (1) the magnetic field gradient is constant across the width of the channel in the x-direction, (2) the magnetic field is constant across the height of the channel in the z-direction, (3) the magnetic force in the y-direction is much smaller than the Stokes drag on the particle, and (4) the source flow and collection flow have similar fluid viscosity $\eta$. In Equation (1), $X_{initial}$ is the distance of the particle from the source flow side of channel wall before entering the magnetic field, D is the particle's effective diameter, $L_y$ is the span of the magnetic field in the y-direction, and $v_y$ is the particle's flow velocity in the y-direction.

For maximum cleansing of the biological fluid, it is crucial to maximize the separation efficiency of magnetic particles, that is, the percentage of magnetic particles that are moved from the source flow path into the collection stream flow path during passage through the HGMC of the microfluidic channel. On the other hand, it is also very important to minimize the loss of the non-magnetic particles from the source flow path, that is, to minimize the percentage of non-magnetic particles that move into the collection stream flow path during the separation process. In the present invention, there are two possible causes for this loss, namely diffusion and the native magnetic susceptibility of a few cell types, for example, RBCs containing deoxyhemoglobin.

Diffusion in the system of the present invention is determined by $d = \sqrt{D_1 L/\bar{v}}$, where $D_1$ is the diffusion coefficient, d is the diffusion distance, L is the channel length, and $\bar{v}$ is the average flow rate. Diffusion is undesirable for the embodiments described above due to the possible loss of critical biomolecules or cells from biological fluids, for example, blood proteins, platelets, and the like. The diffusion coefficients of the smaller proteins are on the order of 10 μm²/s in water, and they are even smaller in more viscous media. Assuming $D_1 = 30$ μm²/s and the acceptable diffusion distance as 10% of the channel width, the determined maximum time that a fluid volume element should be in the channel is $$L/\bar{v} \leq 3.3 \times 10^8 \, \frac{s}{m^2} \cdot W^2,$$

in which W is channel width. Furthermore, by setting $L_y = kL$ ($0 \leq k \leq 1$) and $v_y \approx \bar{v}$, Equation (1) is converted to:

$$X_{final} \leq \frac{3.3 \times 10^8 k \left(m \frac{d\vec{B}}{dx} \cdot \hat{B}\right) W^2}{3\pi \eta D} \, m \quad (2)$$

RBCs containing deoxyhemoglobin reportedly have a relative magnetic susceptibility in water (or plasma) of about $3.9 \times 10^{-6}$. (Melville et al., 1975b; Takayasu et al., 1982). To prevent the loss of RBCs from the source flow path in the system of the present invention, the acceptable deviation of deoxyhemoglobin RBCs in the x-direction after passing through the magnetic field ($X_{final,RBC} - X_{initial,RBC}$) was set to 1/100 of the channel width, that is, W/100.

Design Development

For a magnetic particle at given flow conditions, Equation (1) indicates that $X_{final}$ is a function of m and $$\frac{d\vec{B}}{dx} \cdot \hat{B}.$$

When a magnetic particle is unsaturated $\vec{m} = \chi V \vec{B}/\mu_0$, where $\chi$ is the magnetic permeability of the particle, V is the volume of the particle, and $\mu_0$ is the magnetic permeability of vacuum. As B increases, m approaches a saturation value $m_s$. For convenience, the value of $m_s \mu_0 / \chi V$ is referred to as the saturation magnetic field of the particle $B_s$.

The majority of bioorganisms are non-magnetic, and need to be labeled with superparamagnetic particles in order to be separated from the source mixture. In the system of the present invention, the superparamagnetic particles used to label *E. coli* are 130 nm in diameter, and have a magnetic permeability $\chi_{bead} = 12$ with $B_s$ of 0.02 T. Assuming $\eta = 10^{-3}$ Pa·s (water at 20° C.), $D = 3 \times 10^{-6}$ m (*E. coli*) and $B > B_s$, it was inferred from Equation (2) that to separate *E. coli* bound to a number n of the superparamagnetic particles from the source mixture, $$\frac{d\vec{B}}{dx} \cdot \hat{B} > 0.2/knW \, T/m.$$

Based on their size, an *E. coli* cell surface is estimated to be able to accommodate over 800 of such superparamagnetic particles. If the cut-off value for n is set to 40, that is the system of the present invention needs to remove *E. coli* bound to at least 40 superparamagnetic particles from the source mixture, $$\frac{d\vec{B}}{dx} \cdot \hat{B}$$

should be at least $5.0 \times 10^{-3}/\text{kWT/m}$.

In the system of the present invention, B and $$\frac{d\vec{B}}{dx} \cdot \hat{B}$$

inside the channel are determined by the magnetic properties, geometry, and position of the high gradient magnetic field concentrator magnetic layer and the external magnetic field. Multiple types of magnetic materials may be used to fabricate the magnetic layer. In one embodiment of the present invention, a soft magnetic material (NiFe) with low remnant magnetization was chosen that was magnetized with an external stationary magnet to facilitate rapid and switchable control of separations. The NiFe layer in one embodiment of the present invention has a saturation magnetization ~0.6 T (Rasmussen, 2001). Other magnetic materials may be utilized as the high gradient magnetic field concentrator including paramagnetic materials, permanent magnetic materials, electromagnetic devices, and the like.

Two NiFe layer geometries were selected in the embodiments of the present invention namely, a microneedle as detailed in FIG. 3 and a microcomb as detailed in FIG. 4. The microneedle geometry concentrated the magnetic field at one position along the channel and served as a proof of principle for our fabrication technology and manipulation strategy. The microcomb geometry provided a field gradient along a longer stretch of the microfluidic channel, exposing magnetic particles to force for a longer duration. The magnetic field and field gradient generated by the two NiFe layer geometries were determined by finite element simulations with Maxwell 3D (Ansoft), which solved for magnetic field on a mesh of tetrahedrons that matched the actual device geometry and included the B-H curve of the NiFe layer and the permanent magnet as shown in FIG. 3 and FIG. 4.

In an embodiment of the separation device of the present invention, the NiFe layer was positioned outside the microfluidic channel to eliminate concerns for the biocompatability of the magnetic materials used. FIG. 4 indicates that both B and $$\frac{d\vec{B}}{dx} \cdot \hat{B}$$

depend on the distance between the magnetic layer and the microfluidic channel. It was determined previously that $$\frac{d\vec{B}}{dx} \cdot \hat{B}$$

should be at least $5.0 \times 10^{-3}/\text{kWT/m}$, in which k corresponds to the ratio between the span of the magnetic layer in the y-direction $L_y$ and the microfluidic channel length L. k was set as 0.6 for the microcomb type of magnetic layer to ensure accuracy in device assembly, and the microfluidic channel width W was set as 200 μm. Since $$\frac{d\vec{B}}{dx} \cdot \hat{B}$$

needs to be larger than $5.0 \times 10^{-3}/\text{kW} = 42 \, T/m$, the distance between the layer edge and the collection flow side of channel wall was set to 100 μm. Based on FIG. 4, $$\frac{d\vec{B}}{dx} \cdot \hat{B}$$

inside the channel is approximately 55-250 T/m with $0.017 \, T < B_z < 0.02 \, T$ and $0.024 \, T < B_x < 0.048 \, T$. It was further calculated that assuming $D_{RBC} = 7$ μm, and $\chi_{RBC} = 3.9 \times 10^{-6}$ ($X_{final,RBC} - X_{initial,RBC}$) is less than 0.1 μm, and less than 1/100 of the channel width, confirming that the loss of RBCs from source flow after passing through the magnetic field is negligible.

Finally, for magnetic separations of *E. coli* and other bioorganisms or cells as well, the magnetic susceptible entities in the source mixture include both *E. coli* bound to a wide range number of superparamangetic particles and the superparamagnetic particles themselves. This heterogeneity leads to large variations in $X_{final}$. To minimize such variations as $(X_{final,max} - X_{final,min})/W$, a media with higher fluid viscosity $\eta_c$ was used in the collection stream flow path than in the source flow path ($\eta_s$). By setting $\eta_c = p\eta_s (p > 1)$, Equation (1) is re-written as:

$$X_{final} = \begin{cases} \frac{(m\hat{B} \cdot \nabla \vec{B})L_y}{3\pi\eta D v_y} + X_{initial}, & \text{when } \frac{(m\hat{B} \cdot \nabla \vec{B})L_y}{3\pi\eta D v_y} + X_{initial} \leq \frac{W}{2} \\ \frac{(m\hat{B} \cdot \nabla \vec{B})L_y}{3\pi\eta p D v_y} + \frac{X_{initial}}{p} + \frac{(p-1)W}{2p}, & \text{when } \frac{(m\hat{B} \cdot \nabla \vec{B})L_y}{3\pi\eta D v_y} + X_{initial} > \frac{W}{2} \end{cases} \quad (3)$$

Comparing the variations in $X_{final}$ when media with fluid viscosity of $\eta_s$, and $\eta_c$ are used in the collection stream flow path respectively, and when both $X_{final,max}$ and $X_{final,min}$ are larger than W/2, Equation (3) gives:

$$\frac{(X_{final,max} - X_{final,min})_{\eta_c}}{(X_{final,max} - X_{final,min})_{\eta_s}} = \frac{1}{p} < 1 \quad (4)$$

Hence, using more viscous media in the collection stream flow path can reduce the variations in $X_{final}$. In one embodiment of the present invention, a dextran solution, which is both viscous and biocompatible, was used as the fluid medium for the collection stream flow path.

What is claimed is:

1. An integrated microfluidic separator device comprising:
   a microfluidic channel including:
   a source flow path including a source inlet and a source outlet, and
   a collection stream flow path including a collection outlet, wherein a laminar streamline boundary separates the source flow path and the collection stream flow path, and source flow path is ⅓ to ½ of channel width;
   a-high-gradient magnetic concentrator positioned adjacent to a first side of the microfluidic channel, wherein the high-gradient magnetic concentrator is positioned outside the microfluidic channel, and wherein geometry of the high-gradient magnetic concentrator is adapted to produce a uniform magnetic gradient across the width of the microfluidic channel; and
   a magnetic source to magnetize the high gradient magnetic field concentrator to move magnetically susceptible target material flowing in the source flow path to cross over the laminar streamline boundary and enter the collection stream flow path to separate the magnetically susceptible target material from a fluid flowing in the microfluidic channel.

2. The microfluidic separator device of claim 1, wherein the collection stream flow path includes a viscous dextran solution as a collection media to focus distribution of the magnetically susceptible target material in the collection medium based upon a magnetic deviation distance.

3. The microfluidic separator device of claim 1, wherein the collection stream flow path includes a viscous solution comprising at least one of albumin or lipid solutions as a collection media to focus distribution of the magnetically susceptible target material in the collection medium based upon a magnetic deviation distance.

4. The microfluidic separator device of claim 2, wherein the high curvature geometry of the microfabricated high-gradient magnetic concentrator is a microneedle.

5. The microfluidic separator device of claim 1, wherein the high-gradient magnetic field concentrator comprises permanent magnetic materials that do not require an external magnetizing field.

6. The microfluidic separator device of claim 1, wherein the magnetically susceptible target material is labeled with at least one of paramagnetic particles or super-paramagnetic particles to facilitate separation of the target material from the fluid.

7. The microfluidic separator device of claim 6, wherein the at least one of paramagnetic particles or super-paramagnetic particles bind to the magnetically susceptible target material to facilitate separation of the magnetically susceptible target material from a biological fluid.

8. The microfluidic separator device of claim 7, wherein the separated magnetically susceptible target material includes at least one of microbial or mammalian cells.

9. The microfluidic separator device of claim 7, wherein the separated magnetically susceptible target material includes at least one of molecules or chemicals.

10. The microfluidic separator device of claim 7, wherein the separated magnetically susceptible target material includes at least one of bacterial, viral, or fungal pathogens.

11. The microfluidic separator device of claim 7, wherein the separated magnetically susceptible target material includes at least one of tumor cells or stem cells.

12. The microfluidic separator device of claim 7, wherein the at least one of paramagnetic particles or super-paramagnetic particles are coated with biomolecules and bind to components of the surface of the target material in the fluid.

13. The microfluidic separator device of claim 12, wherein the biomolecules are at least one of proteins, nucleotides, carbohydrates, or lipids.

14. The microfluidic separator device of claim 12, wherein the biomolecules are antibody molecules.

15. The microfluidic separator device of claim 14, wherein the coating of the at least one of paramagnetic particles or super-paramagnetic particles coated with antibody molecules is performed by covalent cross-linking techniques.

16. The microfluidic separator device of claim 14, wherein the biomolecules include natural opsonins.

17. The microfluidic separator device of claim 2, wherein the microfluidic channel and the high-gradient magnetic concentrator are microfabricated on a single chip.

18. The microfluidic separator device of claim 17, wherein the magnetic source is microfabricated on the single chip.

19. The microfluidic separator device of claim 17, wherein the magnetic source is at least one of a permanent magnet, a paramagnetic source, or an electromagnet and is external to the single chip.

20. The microfluidic separator device of claim 17, wherein the microfabricated high-gradient magnetic concentrator comprises permanent magnetic materials that do not require an external magnetizing field.

21. The microfluidic separator device of claim 2, wherein the high-gradient magnetic concentrator includes a layer of magnetizable material.

22. The microfluidic separator device of claim 21, wherein the microfabricated high-gradient magnetic concentrator is magnetized by a paramagnetic magnetic source.

23. The microfluidic separator device of claim 21, wherein the layer of magnetizable material is magnetized using a magnetic source including an electromagnet.

24. The microfluidic separator device of claim 21, wherein the layer of magnetizable material is magnetized using a magnetic source including a permanent magnet.

25. The microfluidic separator device of claim 24, wherein the permanent magnet comprises neodymium.

26. The microfluidic separator device of claim 21, wherein the microfabricated high-gradient magnetic concentrator is positioned outside the microfluidic channel.

27. The microfluidic separator device of claim 21, wherein the microfabricated high-gradient magnetic concentrator is positioned within the microfluidic channel.

28. The microfluidic separator device of claim 26, wherein the microfabricated high-gradient magnetic concentrator positioned outside the microfluidic channel includes a layer of NiFe.

29. The microfluidic separator device of claim 27, wherein the microfabricated high-gradient magnetic concentrator positioned within the microfluidic channel includes a layer of NiFe.

30. The microfluidic separator device of claim 26, wherein the layer of magnetizable material of the microfabricated high-gradient magnetic concentrator is substantially the same thickness as the height of the microfluidic channel to subject the channel to a substantially uniform magnetic field gradient.

31. The microfluidic separator device of claim 21, wherein the position of the microfabricated high-gradient magnetic concentrator and the laminar fluid flow prevents accumulation of collected target material at sidewalls of the channel and thereby provides continuous fluid flow in the microfluidic channel.

32. The microfluidic separator device of claim 2, wherein the magnetically susceptible target material that crosses over the laminar streamline boundary and enters the collection stream flow path exits the microfluidic channel through the collection outlet.

33. The microfluidic separator device of claim 2, wherein material flowing in the source flow path that is not magnetically susceptible exit the microfluidic channel through the source outlet.

34. The microfluidic separator device of claim 2, wherein the high-gradient magnetic concentrator provides a horizontal magnetic field of at least 0.025 T and a vertical magnetic field of at least 0.018 T and a field gradient of at least 50 T/m.

35. The microfluidic separator device of claim 2, wherein the separated target material includes microbial cells.

36. The microfluidic separator device of claim 35, wherein the microbial cells are *E. coli* bacteria.

37. The microfluidic separator device of claim 35, wherein the microbial cells are *Candida Albicans* fungi.

38. The microfluidic separator device of claim 2, wherein the separated target material includes mammalian cells.

39. The microfluidic separator device of claim 38, wherein the mammalian cells include tumor cells.

40. The microfluidic separator device of claim 38, wherein the mammalian cells include stem cells.

41. The microfluidic separator device of claim 38, wherein the mammalian cells include blood cells.

42. The microfluidic separator device of claim 35, wherein the microbial cells are labeled with at least one of biocompatible paramagnetic particles or biocompatible super-paramagnetic particles to facilitate separation of the microbial cells from a biological fluid.

43. The microfluidic separator device of claim 38, wherein the mammalian cells are labeled with at least one of biocompatible paramagnetic particles or biocompatible super-paramagnetic particles to facilitate separation of the mammalian cells from a biological fluid.

44. The microfluidic separator device of claim 7, wherein the biological fluid includes at least one of blood, serum, urine, cerebrospinal fluid, trachea aspirates, saliva, tears, or perspiration.

45. A microfluidic separator system comprising a plurality of integrated microfluidic separator devices included to provide multiplexing separation of target material from a fluid, and wherein each microfluidic separator device includes:
a microfluidic channel including:
a source flow path including a source inlet and a source outlet, and
a collection stream flow path including a collection outlet, wherein a laminar streamline boundary separates the source flow path and the collection stream flow path, and source flow path is ⅓ to ½ of channel width;
a high-gradient magnetic concentrator positioned adjacent to a first side of the microfluidic channel, and wherein geometry of the high-gradient magnetic concentrator is adapted to produce a uniform magnetic gradient across the width of the microfluidic channel; and
a magnetic source to magnetize the high gradient magnetic field concentrator to move magnetically susceptible target material flowing in the source flow path to cross over the laminar streamline boundary and enter the collection stream flow path to separate the magnetically susceptible target material from a fluid flowing in the microfluidic channel.

46. The microfluidic separator device of claim 1, wherein the high-gradient magnetic concentrator is a microcomb and the high-gradient magnetic concentrator is positioned outside the microfluidic channel.

47. The microfluidic separator device of claim 1, wherein the high gradient magnetic concentrator is microfabricated.

48. The microfluidic separator device of claim 1, wherein the high gradient magnetic concentrator has a high curvature geometry.

49. The microfluidic separator device of claim 48, wherein the high curvature geometry of the high-gradient magnetic field concentrator includes a magnetic line array.

50. The microfluidic separator device of claim 48, wherein the high curvature geometry of the high-gradient magnetic concentrator is a microcomb.

51. The microfluidic separator device of claim 50, wherein the high-gradient magnetic concentrator microcomb includes a triangular saw-tooth configuration.

52. The microfluidic separator device of claim 50, wherein the microcomb has the dimensions of 3.8 mm in X, 12 mm in Y, 50 μm in Z with teeth 300 μm in X and spaced by 200 μm in Y.

* * * * *